United States Patent [19]

Tanimoto et al.

[11] Patent Number: 6,071,542
[45] Date of Patent: Jun. 6, 2000

[54] ANTIBACTERIAL ZEOLITE CAUSING LITTLE DISCOLORATION AND METHOD OF THE PRODUCTION THEREOF

[75] Inventors: Takeo Tanimoto, Hyogo; Noboru Watanabe, Fukui; Kazuhiko Nakashima; Ryuhei Matsuo, both of Osaka; Manabu Nagata, Hyogo; Yuji Shingai, Hyogo; Tatsuo Otani, Hyogo, all of Japan

[73] Assignee: Kanebo Ltd., Tokyo, Japan

[21] Appl. No.: 08/913,862

[22] PCT Filed: Mar. 15, 1996

[86] PCT No.: PCT/JP96/00693

§ 371 Date: Nov. 13, 1997

§ 102(e) Date: Nov. 13, 1997

[87] PCT Pub. No.: WO96/28028

PCT Pub. Date: Sep. 19, 1996

[30] Foreign Application Priority Data

Mar. 16, 1995 [JP] Japan ........................................ 83501

[51] Int. Cl.$^7$ .............................. A01N 59/16; C08K 3/34; C08K 9/06; C09C 1/40
[52] U.S. Cl. .......................... 424/618; 423/700; 424/617; 424/630; 424/641; 424/644; 424/646; 424/650; 424/652; 424/653; 424/654; 424/655; 424/682; 514/970; 514/972
[58] Field of Search ..................... 424/682, 684, 424/689, 691, 600, 617, 618, 630, 641, 644, 646, 650, 652, 653, 654, 655; 514/970, 972, 770; 423/700

[56] References Cited

U.S. PATENT DOCUMENTS

| | | | |
|---|---|---|---|
| 4,775,585 | 10/1988 | Hagiwara et al. | 428/323 |
| 4,801,445 | 1/1989 | Fukui et al. | 424/69 |
| 4,935,483 | 6/1990 | Gamon et al. | 528/31 |
| 4,959,268 | 9/1990 | Hagiwara et al. | 428/403 |
| 5,661,196 | 8/1997 | Mayer et al. | 523/122 |

FOREIGN PATENT DOCUMENTS

| | | |
|---|---|---|
| 1061158 | 7/1952 | France . |
| 63-260810 | 10/1988 | Japan . |
| 63-265809 | 11/1988 | Japan . |
| 63-270764 | 11/1988 | Japan . |
| 3-131513 | 6/1991 | Japan . |
| 3-164423 | 7/1991 | Japan . |
| 3-197313 | 8/1991 | Japan . |
| 3-242317 | 10/1991 | Japan . |
| 3-80814 | 12/1991 | Japan . |
| 4-292412 | 10/1992 | Japan . |
| 5-156164 | 6/1993 | Japan . |

OTHER PUBLICATIONS

Tanimoto et al., JP406247816A, Production of antimicrobial zeolite reduced in discoloration action, Sep. 6, 1994, Messenger APS online, Abstract.

*Primary Examiner*—John Pak
*Assistant Examiner*—Frank Choi
*Attorney, Agent, or Firm*—Cowan, Liebowitz & Latman, P.C.; William H. Dippert

[57] ABSTRACT

The present invention provides antibacterial zeolite exhibiting a less discoloring action, obtained by treating the surface of zeolite supporting an antibacterial metal with 0.5 to 20% by weight, based on said zeolite, of a composition comprising (A) 100 parts by weight of a hydrolyzable silane and/or oligomer thereof which comprises 10 to 100% by weight of a hydrolyzable silane and/or oligomer thereof having an aryl group; (B) 1 to 1000 parts by weight of an organopolysiloxane having a basic nitrogen atom; and (C) 0.2 to 250 parts by weight of an acid which is soluble in water and which can form a salt with the aforesaid (B). The present antibacterial zeolite exhibits a remarkably less action of discoloring an organic polymer which contains the antibacterial zeolite when the polymer blend is placed under the influence of heat or the sunshine.

8 Claims, No Drawings

ANTIBACTERIAL ZEOLITE CAUSING LITTLE DISCOLORATION AND METHOD OF THE PRODUCTION THEREOF

This application is a 371 of PCT/JP96/00693, filed on Mar. 15, 1996.

FIELD

The present invention relates to antibacterial zeolite exhibiting a less action of discoloring an organic polymer containing the antibacterial zeolite when the polymer composition is placed under the influence of heat or the sunshine, and to a process for the preparation of the same.

BACKGROUND

It has been known for a long time that silver ion, copper ion, or zinc ion, etc. has antibacterial properties. For example, the silver ion has been widely used in the form of a solution of silver nitrate as a disinfectant or antibacterial agent. However, such a solution form is inconvenient for handling and restricted in use. In order to eliminate these disadvantages, a product in which metal ions are supported in a solid such as zeolite was developed. For example, French Patent Application No. 1,061,158 describes paint for ships containing 20 to 30% by weight of zeolite which is saturated with copper, zinc or silver. In Japanese Patent Publication No. Sho-63-54013/1988, Japanese Patent Application Laid-Open Nos. Sho-63-260810/1988 and Sho-63-270764/1988, there is described a zeolite composition in which antibacterial properties are further improved.

There was proposed antibacterial zeolite which did not discolor by ultraviolet light such as the sunshine with the passage of time (Japanese Patent Application Laid-Open No. Sho-63-265809/1988). This application relates to antibacterial zeolite in which a part or the whole of ion-exchangeable ions in the zeolite is substituted with ammonium ions and antibacterial metal ions and to an antibacterial polymer composition. However, this antibacterial zeolite has some disadvantages. That is, the zeolite is lacking in heat stability when only silvers are supported as the antibacterial metal. The zeolite itself discolors to become mud yellow color when heated to 300° C., particularly when A-type zeolite is used. Therefore, when it is kneaded into a polypropylene resin at a kneading temperature of 240° C., it makes the resin light brown. This disadvantage causes the zeolite to lose its commercial value.

It is known that antibacterial zeolite particles having silicone-type coating may be prepared by treating the antibacterial zeolite particles with a solution of a silicone-type coating agent (Japanese Patent Publication No. Hei-3-80814/1991). In these particles, their hygroscopic property is suppressed to a degree needed. They have hydrophobic property or water repellent property. Accordingly, these particles have an advantage that molding may be advantageously carried out because they do not release water when they are blended with an organic polymer to be molded.

DISCLOSURE OF THE INVENTION

A purpose of the present invention is to provide such antibacterial zeolite that when the zeolite is blended with organic polymers, particularly with high performance engineering plastic polymers having high melting points such as ABS resins, polyester resins and polyamide resins, or with paper, the zeolite makes the organic polymer composition quite less discolored under the influence of heat during processing or under ultraviolet light such as the sunshine, and to provide a process for the preparation of the same.

The present inventors have found that the particular composition which will be described below penetrates into micropores of zeolite well and then may cover the surface of the zeolite completely. We have also found that when a predetermined amount of the aforesaid composition is used, the discoloration may be effectively suppressed without decreasing the intrinsic antibacterial properties that the antibacterial zeolite has. These findings lead to the completion of the invention.

That is, the present invention is antibacterial zeolite exhibiting a less discoloring action, obtained by treating the surface of zeolite supporting an antibacterial metal with 0.5 to 20% by weight, based on said zeolite, of a composition comprising (A) 100 parts by weight of a hydrolyzable silane and/or oligomer thereof which comprises 10 to 100% by weight of a hydrolyzable silane and/or oligomer thereof having an aryl group; (B) 1 to 1000 parts by weight of an organopolysiloxane having a basic nitrogen atom; and (C) 0.2 to 250 parts by weight of an acid which is soluble in water and which can form a salt with the aforesaid (B).

If antibacterial zeolite is impregnated merely with a commercially available polysiloxane dissolved in a solvent, as described in the aforesaid Japanese Patent Publication No. Hei-3-80814/1991, it is considered that the polysiloxane is deposited only on the relatively outer surface of the porous zeolite to form coating. However, it is considered that when the composition according to the invention which comprises the aforesaid (A), (B) and (C) is used to treat antibacterial zeolite (which is hydrophilic) dispersed in an aqueous medium, the aforesaid composition penetrates well into macropore of the porous zeolite and forms a thin film consisting of the aforesaid composition precisely along the irregular surface of the zeolite to coat the surface of the antibacterial zeolite completely, particularly due to the improvement in permeability and adhesion of the composition. Accordingly, such a coating is considered not to be peeled when it is kneaded with an organic polymer, unlike a mere surfacecoating by deposition. The composition comprising the antibacterial zeolite which has been thus treated and an organic polymer is less discolored even at high temperatures above the melting point of the polymer.

The present invention will be further specifically described below.

Antibacterial metal-supporting zeolite is known per se and may be prepared by ion-exchanging zeolite with antibacterial metals. Examples of the antibacterial metals include silver, copper, zinc, mercury, tin, lead, bismuth, cadmium, chromium, cobalt, nickel, or a combination of two or more of these metals. Preference is given to silver, copper, zinc, or a combination of these. Particularly, silver alone or a combination of silver with copper or zinc is excellent in antibacterial properties. Particularly in the case of the antibacterial zeolite supporting silver, discoloration of the organic polymer under the action of heat or light would be relatively high. In such a case, the effect of the invention is remarkable. Methods for preparing antibacterial zeolite are described in, for example, Japanese Patent Publication Nos. Sho-63-54013/1988 and Hei-3-80814/1991.

Zeolite is generally aluminosilicate having a three dimensionally grown skeleton structure and is generally represented by $xM_{2/n}O \cdot Al_2O_3 \cdot ySiO_2 \cdot zH_2O$, written with $Al_2O_3$ as a basis, wherein M represents an ion-exchangeable metal ion, which is usually the ion of a monovalent or divalent metal; n corresponds to the valence of the metal; x is a coefficient of the metal oxide; y is a coefficient of silica; and z is the number of water of crystallization. There are known various kinds of zeolites having different component ratios, fine pore diameters, and specific surface areas.

As the zeolite used in the present invention, any natural or synthetic zeolites can be used.

Examples of natural zeolite includes analcime, chabazite, clinoptilolite, erionite, faujasite, mordenite, and phillipsite. On the other hand, typical examples of synthetic zeolite include A-type zeolite, X-type zeolite, Y-type zeolite, and mordenite. These synthetic zeolite are preferably used as the zeolite in the present invention. Particularly, synthetic A-type zeolite is preferred. In this zeolite, discoloration is considerable and, therefore, the present effect would be remarkable.

The shape of zeolite may preferably be powdery particulate. A particle size of the zeolite can suitably be selected depending on application fields. When the present antibacterial zeolite is mixed to a molded article having a relatively thickness, for example, various types of containers, pipes, particles or coarse fibers, the particle size may be in the range of a few microns to several tens microns or even above several hundreds microns. Meanwhile, when fine fibers or films are molded, a smaller size of particle is preferred. For example, the particle size of 5 microns or less, especially 2 microns or less is preferred for fibers to be used in clothes. Also when the present zeolite is used for synthetic paint such as home paint or various kinds of synthetic resin adhesives, a smaller size of particle is preferred.

The metal is preferably supported on solid particles of zeolite through an ion-exchange reaction. If metal ions are merely adsorbed or attached without the ion-exchange reaction, keeping the antibacterial effect is apt to be poor in the final products. Zeolite is preferably ion-exchanged with metal ions in an amount of less than an ion-exchangeable amount of the zeolite particles, particularly in an amount of about 90% or less thereof. In the zeolite ion-exchanged in an amount of more than its saturated amount, the antibacterial effect and durability thereof is sometimes poor.

As a method for supporting metal ions, some cases where various kinds of zeolites are converted to Ag-zeolite will be described. An aqueous solution of a water-soluble silver salt such as silver nitrate is usually used at the conversion to Ag-zeolite and in this case the concentration and pH must be sufficiently taken care of. For example, if the silver ion concentration is too high (for example, when 1 to 2 M of $AgNO_3$ are used) in the case of converting an A-type zeolite or an X-type zeolite (sodium-type zeolite) into a zeolite supporting silver ions through an ion-exchange reaction, the silver ion in the solution sometimes forms silver oxide in the solid phase of the zeolite as precipitates simultaneously when the silver ion is replaced with the sodium ion in the solid phase of the zeolite through an ion-exchange reaction. It is known that the antibacterial properties decrease when the silver oxide precipitates. In order to prevent such a formation of the precipitates, it is preferred to keep the concentration of the silver solution in a diluted condition, for example, 0.3 M or less or to add acids to the solution during the ion-exchange to adjust the pH of the solution to the acidic side. When silver nitrate of such a concentration is used or the pH of the solution is kept in the acidic side, antibacterial effect may be exhibited in the optimum conditions.

When the aforesaid ion-exchange reaction is performed in a batch method, the zeolite may be soaked in a metal salt solution having the concentration or the acidic pH as mentioned above. In order to increase the metal content in the zeolite, the batch treatment may be repeated. Meanwhile, in the case of treating the zeolite in a column method using a metal salt solution having the aforesaid concentration or pH, the intended metal-zeolite may be easily obtained by packing the zeolite in an adsorption column and passing the solution of the metal salt through the column.

The amount of the metal incorporated in the aforesaid metal-zeolite may be preferably 20% by weight or less, particularly 0.001 to 5% by weight in the case of silver, based on anhydrous zeolite plus metal. In the case of zinc or copper, the amount of zinc or copper incorporated in the metal-zeolite may be preferably 25% by weight or less, particularly 0.01 to 15% by weight, based on anhydrous zeolite plus metal. It is possible to use two or more of silver, copper, zinc and the other metal ions together. In this case, although the total amount of the metal ions is dependent on the composition of the metal ions, it may be preferably 25% by weight or less, particularly 0.001 to 15% by weight, based on anhydrous zeolite plus metal.

It is possible to increase the discoloration- suppressing effect without preventing the bactericidal effect preferably by incorporating the other metal ions than the antibacterial metal ions, for example, sodium, potassium, magnesium, calcium, aluminum, titanium, cerium and other metal ions. Accordingly, these ions may remain or co-exist.

After the ion-exchange reaction, the zeolite is generally separated from the liquid and washed. The separation may be carried out by any methods such as filtration or decantation. Any washing method may be carried out. For example, the zeolite may be washed with a small amount of distilled water. The zeolite after washed may be optionally subjected to drying treatment. The drying conditions are preferably under normal or reduced pressure at 100 to 500° C., particularly under reduced pressure at 100 to 350° C. It is possible to omit the drying treatment and to carry out the next procedure.

The zeolite supporting antibacterial metals, hereinafter referred to as antibacterial zeolite for short, is treated with the composition composed of (A), (B) and (C) according to the invention. The treatment is preferably carried out in a dispersion of antibacterial zeolite in an aqueous medium, preferably water. In the case where the ratio of component (A) is high, it is preferred to use water-soluble organic solvents, preferably alcohols such as isopropyl alcohol, in addition to water. In general, an aqueous dispersion of synthetic zeolites and, accordingly, an aqueous dispersion of antibacterial zeolite, exhibits strong alkalinity. Even if an acid is added to the aqueous dispersion to neutralize it, it also exhibits strong alkalinity after several hours or after one day. The treatment with the composition according to the present invention is carried out preferably at less than pH 7, more preferably pH 6.5 or less.

The composition according to the invention is susceptible to hydrolysis under the presence of either alkali or acid to cause polycondensation reaction. However, it has been found that in the surface treatment on antibacterial zeolite, the treatment at less than pH 7 leads to remarkably less discoloration by heat or light of an organic polymer with which the zeolite is blended, compared to the treatment under the alkaline conditions. This is considered to be due to the fact that in the treatment at less than pH 7, a thin film of the composition according to the invention adheres more strongly to the surface of the antibacterial zeolite and, therefore, is peeled with more difficulty when the zeolite is kneaded with the organic polymer. Accordingly, it is preferred to soak the zeolite in an aqueous acidic solution in advance to neutralize alkaline components bleeding from the synthetic zeolite. Consequently, it is preferred to add the acid to maintain the pH at less than 7 before or during the treatment.

To this end, it is preferred to carry out acid-soaking, preferably before, after or simultaneously with having the antibacterial metals supported, according to the methods described in Japanese Patent Application Laid-Open Nos. Hei-3-197313/1991, Hei-3-131513/1991, Hei-3-164423/1991 and Hei-3-242317/1991 and Japanese Patent Application No. Hei-2-297841/1990. These methods are basically carried out as follows synthetic zeolite is soaked in an acidic aqueous solution; and while an acid is replenished to the soaking solution to maintain the pH at a predetermined value of about 7 or less, preferably 4.5 to 7.0, particularly 5.0 to 6.5, the soaking is continued until the pH stays almost constant for at least 0.5 hour without further replenishing the acid. Next, the synthetic zeolite is washed or not, and dried or not and, then, used in a next step.

The acidic aqueous solution used for soaking the synthetic zeolite is an aqueous solution of inorganic acid and/or organic acid. For example, use may be made of inorganic acids such as hydrochloric acid, sulfuric acid, nitric acid and phosphoric acid; and organic acids such as formic acid, acetic acid, oxalic acid and tartaric acid. Among these, preference is given to weak acids such as acetic acid, formic acid, tartaric acid, adipic acid and boric acid. In addition, it is preferred to add a buffer to the acid aqueous solution. The buffer may be one which gives a buffering effect to the acid aqueous solution. Typical examples of the buffer include combinations of various weak acids with their salts, for example, acetic acid with sodium acetate, potassium acetate or ammonium acetate; oxalic acid with sodium oxalate, potassium oxalate or ammonium oxalate; tartaric acid with sodium tartrate, potassium tartrate or ammonium tartrate; and phosphoric acid with sodium phosphate, potassium phosphate or ammonium phosphate, but are not restricted to these. Two or more acids and/or buffers may be used in mixture.

A certain degree of the effect may be obtained by washing the zeolite in place of the aforesaid soaking, but the degree of the effect is small. In natural zeolite, it is not necessary to subject the zeolite to the aforesaid soaking or washing because it does not exhibit alkalinity originally.

In the present invention, the composition used for treating the surface of antibacterial zeolite is composed of (A) 100 parts by weight of a hydrolyzable silane and/or oligomer thereof which comprises 10 to 100% by weight of a hydrolyzable silane and/or oligomer thereof having an aryl group; (B) 1 to 1000 parts by weight of an organopolysiloxane having a basic nitrogen atom; and (C) 0.2 to 250 parts by weight of an acid which is soluble in water and which can form a salt with the aforesaid (B).

As components (A), (B) and (C) which compose the aforesaid composition, use may be made of those described in Japanese Patent Application Laid-Open No. Hei-5-156164/1993.

Component (A) is a compound represented by the following general formula (I) preferably with a molecular weight of about 600 or less (this is multiplied in the case of the oligomer):

$$R^1_n\text{-Si-}(OR^2)_{4-n} \tag{I}$$

wherein $R^1$ independently represents a $C_1$ to $C_{18}$ saturated alkyl group, aryl group or aralkyl group ; $R^2$ independently represents a $C_1$ to $C_6$ saturated alkyl group, particularly methyl, ethyl and propyl groups; and n is 1 or 2.

Among component (A), a hydrolyzable silane having an aryl group means those in which at least one of $R^1$ in the general formula (I) is an aryl group. Preferred examples include phenyltrimethoxysilane, phenyltriethoxysilane, diphenyldimethoxysilane, diphenyldiethoxysilane, etc.

Among component (A), the hydrolyzable silane having no aryl group preferably includes methyltrimethoxysilane, methyltriethoxysilane, methyltripropoxysilane, ethyltrimethoxysilane, ethyltriethoxysilane, ethyltripropoxysilane, propyltrimethoxysilane, propyltriethoxysilane, propyltripropoxysilane, butyltrimethoxysilane, butyltriethoxysilane, hexyltrimethoxysilane, hexyltriethoxysilane, benzyltrimethoxysilane, octyltrimethoxysilane, octyltriethoxysilane, octyltripropoxysilane, decyltrimethoxysilane, dodecyltrimethoxysilane, octadecyltrimethoxysilane, tetradecyltrimethoxysilane, tetradecyltriethoxysilane, hexadecyltrimethoxysilane, hexadecyltriethoxysilane, dimethyldimethoxysilane, dimethyldiethoxysilane, dibutyldimethoxysilane, etc.

Alternatively, a condensed dimer or trimer or higher oligomers of the aforesaid silane may be used. The oligomers may be used as long as they are hydrolyzable. Preference is given to octadecamer or lower oligomers of the aforesaid silane.

In component (A), the amount of the hydrolyzable silane and/or oligomer thereof having an aryl group is at least 10% by weight, preferably at least 25% by weight, particularly at least 35% by weight, and at most 100% by weight, preferably at most 90% by weight, particularly at most 80% by weight. If the amount is less than the aforesaid lower limit, the present effect is less exhibited.

The organopolysiloxane having a basic nitrogen atom used as component (B) is a compound composed of the unit represented by the following general formula (II):

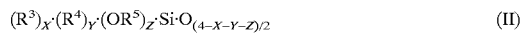

$$(R^3)_X \cdot (R^4)_Y \cdot (OR^5)_Z \cdot \text{Si-O}_{(4-X-Y-Z)/2} \tag{II}$$

wherein $R^3$ independently represents a hydrogen atom or a $C_1$ to $C_8$ saturated alkyl group; $R^4$ independently represents an N-substituted or unsubstituted aminoalkyl group; $R^5$ independently represents a hydrogen atom or a $C_1$ to $C_6$ saturated alkyl group X, Y and Z are averaged values, X is 0 to 3, preferably 0 to 2, Y is 0.01 to 1, preferably 0.1 to 0.6, Z is 0 to 3, preferably 0 to 0.8, and the sum of X, Y and Z is 3.4 or less.

This organopolysiloxane having a basic nitrogen atom may be prepared by mixing and heating polysiloxane having an H—Si bond with alkoxysilane having an amino group to react them.

In general, commercially available polysiloxane having an H—Si bond may be used. Examples of them include polydimethylsiloxane with a terminal hydrogen (PS-557, ex Chisso Corporation), polymethylhydrosiloxane end-capped with a trimethylsiloxy group (PS-118, ex Chisso Corporation), polymethyl hydrogen-dimethylsiloxane copolymer (PS-122.5, ex Chisso Corporation), polymethyl hydrogen-methyloctylsiloxane copolymer (PS-125, ex Chisso Corporation) and polyethyl hydrogen siloxane (PS-128, ex Chisso Corporation).

Preferred alkoxysilane having an amino group is represented by the following general formula (III):

$$(R^6)_P (R^4) \text{Si} (OR^5)_{3-P} \tag{III}$$

wherein $R^4$ and $R^5$ each represent the same meaning as mentioned above; $R^6$ is a $C_1$ to $C_8$ saturated alkyl group; and P is 0 or 1.

Examples of $R^4$ include an N-substituted aminoalkyl group such as $CH_3 \cdot NH(CH_2)_3$—, $CH_3 \cdot NH(CH_2)_5$—, $NH_2 \cdot (CH_2)_2 NH(CH_2)_3$—, $C_4H_9 \cdot NH(CH_2)_2 \cdot NH \cdot (CH_2)_3$—; or an unsubstituted aminoalkyl group such as $H_2N(CH_2)_2$—, $H_2N(CH_2)_3$—.

As the alkoxysilane having an amino group, use may be preferably made of N-(2-aminoethyl)-3-aminopropyltrimethoxysilane, N-(2-aminoethyl)-3-aminopropylmethyldimethoxysilane, etc., which are commercially available.

Component (B), organopolysiloxane having a basic nitrogen atom, forms a salt with the water soluble acid (C) to improve its hydrophilicity, by which the hydrolysis of component (A), hydrolyzable silane and/or oligomer thereof, is enhanced. Component (B) also has an action of dispersing these hydrolysates in an aqueous medium.

The amount of component (B) used in the invention is preferably at least 1 part by weight, more preferably at least 10 parts by weight, particularly at least 20 parts by weight, and preferably at most 1000 parts by weight, more preferably at most 200 parts by weight, particularly at most 100 parts by weight, per 100 parts by weight of component (A). If the amount is less than the aforesaid lower limit, good dispersion of the composition composed of components (A), (B) and (C) in an aqueous medium, preferably water, may not be obtained in the surface-treatment on the antibacterial zeolite. This is undesirable. It is preferred to use component (B) in such an amount that good dispersion of the composition in water is obtained because the treatment according to the invention is conveniently carried out in a water-based medium. Meanwhile, if the amount of (B) exceeds the aforesaid upper limit, the present effect, that is, the discoloration-suppressing effect decreases. This is undesirable.

As the water-soluble acid as component (C), use may be made of at least one acid selected from known ones such as hydrochloric acid, sulfuric acid, nitric acid, phosphoric acid, acetic acid, and propionic acid. Among these, acetic acid and propionic acid are advantageous. The amount of component (C) used in the invention is at least 0.2 part by weight, preferably at least 2 parts by weight, particularly at least 5 parts by weight, and at most 250 parts by weight, preferably at most 50 parts by weight, particularly at most 40 parts by weight, per 100 parts by weight of component (A). If the amount is less than the aforesaid lower limit, dispersion of the composition in water deteriorates. Meanwhile, if it exceeds the aforesaid upper limit, the discoloration-suppressing effect decreases. Meanwhile, the weight ratio of component (C) to component (B) is preferably at least 0.0002, more preferably at least 0.005, particularly at least 0.05, and preferably at most 250, more preferably at most 100, particularly at most 10.

In the present invention, the amount of the composition comprising the aforesaid components (A), (B) and (C) is at least 0.5% by weight, preferably at least 1.0% by weight, particularly at least 2.0% by weight, and at most 20% by weight, preferably at most 16% by weight, particularly at most 14% by weight, based on the amount of antibacterial zeolite. If the amount is less than the aforesaid lower limit, the discoloration action of antibacterial zeolite is not suppressed. Meanwhile, if it exceeds the aforesaid upper limit, the antibacterial zeolite cannot maintain its antibacterial properties. This is undesirable.

In the surface treatment of antibacterial zeolite, the composition comprising the aforesaid components (A), (B) and (C), preferably in the form of a mixture with an aqueous medium, preferably water, is added to an aqueous dispersion of zeolite. In addition to water, use may be made of water soluble organic solvents, preferably alcohol such as methyl alcohol, ethyl alcohol and isopropyl alcohol together with water. Alternatively, these organic solvents may be used alone. For any of the above solvents, the aforesaid silicone composition is used in a diluted state to, preferably, 1 to 30% by weight, particularly 0.5 to 20% by weight.

In order to enhance the dispersion of the present composition comprising the aforesaid components (A), (B) and (C) in an aqueous medium, surfactants may be added in the medium. However, it is preferred to use it in a minimum amount needed because the addition of the surfactant decreases adhesion ability of the composition to the surface of zeolite. Preferable surfactants include, for example, ether type, alkylphenol type, ester type, sorbitan ester type, sorbitan ester ether type, acetylene type and silicone type nonionic surfactants described in Japanese Patent Application Laid-Open No. Hei-5-156164/1993.

As a curing reaction-enhancing agent for the composition according to the invention, catalysts may be added. Types of the catalysts are not restricted to particular ones. Preference is given to organic tin compounds and organic titanium compounds.

In the preferred embodiments of the treatment with the composition according to the invention, antibacterial zeolite to which antibacterial metals have been applied in an aqueous medium, preferably water, is separated from the aqueous medium. Then the antibacterial zeolite in wet conditions after washed and before dried, or that after dried is dispersed in an aqueous medium, preferably water, again. In general, the antibacterial zeolite is dispersed in an aqueous medium, preferably water, the amount of which is preferably equal to or more than the amount of the antibacterial zeolite, particularly twice or more of it. The surface treatment of zeolite is carried out, preferably with stirring the dispersion, preferably at a temperature from room temperature to 80° C., by gradually adding the composition according to the invention which is preferably of the form of homogeneous dispersion in another aqueous medium, preferably in water, to the dispersion of the aforesaid zeolite in the aqueous medium. A treating time may be preferably selected in a range of 0.5 to 48 hours, with the treatment at a low temperature for a long time being preferred.

After the completion of the surface treatment as mentioned above, the antibacterial zeolite on which the surface treatment has been applied is separated and then washed and dried. The separating operations may be carried out in any manner such as filtration and decantation. The washing may be omitted. The drying treatment is carried out under normal pressure or reduced pressure at a temperature of preferably 100 to 500° C., more preferably 150 to 500° C., particularly 200 to 500° C. Particularly, it is preferred to carry out it at 100 to 350° C. under reduced pressure. The drying temperature is preferably not lower than a melting point of the organic polymer which will be kneaded with the present antibacterial zeolite, more preferably not lower than a kneading temperature and not higher than 500° C. Thus the antibacterial zeolite which exhibits very little discoloration is obtained. Because the kneading of the antibacterial zeolite and the molding are carried out preferably at 200 to 240° C. with, for example, polypropylene resin, at 220 to 260° C. for ABS resin, at 240 to 280° C. for polyamide resin, or at 260 to 300° C. for polyester resin, a temperature of the aforesaid lower limit or higher and the aforesaid upper limit or lower may be chosen.

It is considered that a thin film of the composition according to the invention is formed on the surface of the antibacterial zeolite in the present treatment. However, the antibacterial properties are not inhibited by the treatment. The antibacterial zeolite treated with the composition according to the invention of an amount of at most 20% by weight based on the antibacterial zeolite exhibits comparable or practically satisfactory antibacterial properties, compared to those of the antibacterial zeolite which is not treated so.

The amount of the composition according to the invention of 0.5% by weight or more based on the antibacterial zeolite may suppress the discoloration. That is, in the present invention, when zeolite is surface-treated with 0.5 to 20% by weight of the composition according to the invention based on the antibacterial zeolite, the antibacterial zeolite may be obtained which exhibits the effect of less discoloration, while maintaining excellent antibacterial properties.

To the present antibacterial zeolite may be added white pigments such as magnesium oxide, calcium oxide, aluminum oxide, zinc oxide, titanium oxide, silicon dioxide, calcium carbonate, magnesium carbonate and barium sulfate before or after surface-treated with the composition according to the invention in order to add to whiteness.

In addition, to the present antibacterial zeolite may be added additives such as magnesium silicate, aluminum silicate, zinc silicate, silica gel-zinc, synthetic hydrotalcite, aluminum tripolyphosphate before or after surface-treated with the aforesaid composition. These additives do not inhibit the present effects.

The antibacterial zeolite obtained in the present invention may be used in the same fields as those of the prior art antibacterial zeolite. Particularly, it is blended with any low molecular weight or high molecular weight organic polymers to exhibit its antibacterial properties while the organic polymer blend does not discolor. Even for engineering plastics having a high melting point which had a problem of discoloration in the prior art, such as ABS resins and polyester resins, the antibacterial zeolite obtained in the present invention does not cause the polymer blend to discolor. The organic polymer includes, for example, thermoplastic synthetic high polymers such as polyethylene, polypropylene, polystyrene, polyvinyl chloride, polyvinylidene chloride, polyamide, polyester, polyester elastomers, polyvinyl alcohol, polycarbonate, polyacetal, ABS resin, acryl resin, vinyl acetate resin, fluorocarbon resin and polyurethane; thermosetting synthetic high polymers such as phenol resin, urea resin, melamine resin, unsaturated polyester resin, epoxy resin and urethane resin; and regenerated or semi-synthetic high polymers such as rayon, cupra, acetate and triacetate. The antibacterial zeolite may be blended to paper materials in paper making. When the prior art antibacterial zeolite, particularly silver-supporting synthetic zeolite, is blended in polyolefin such as polyethylene and polypropylene which have a remaining catalyst and reactive terminal groups, or engineering plastics such as ABS resin, polyamide and polyester which are processed at high temperatures because of their particularly high melting points, discoloration may easily occur by heat during the molding and processing or ultraviolet light such as the sunshine in use. However, when the present antibacterial zeolite is used, discoloration is remarkably suppressed.

The antibacterial zeolite obtained in the present invention itself exhibits high whiteness and, therefore, has high commercial value. In addition, the present antibacterial zeolite is dispersed well in organic high molecular weight resins and may be kneaded in them. Accordingly, it is suitably used in foods, medicines and sanitary and environmental fields, for example, in the form of fibers, films and other molded articles. Because the antibacterial zeolite itself has high safety and is stable, it may be applied to polymers widely used in various fields including paints, adhesives, pressure sensitive adhesives and may, therefore, extremely enhance their cleanliness and comfortableness. The present antibacterial zeolite may also be used with other antibacterial agents and anti-fungus agents, particularly organic antibacterial agents and anti-fungus agents. It is also possible to use it with other organic insecticides.

The present invention will be elucidated more specifically with reference to the following Examples. The present invention should not be limited to these Examples.

EXAMPLE

Examples 1 to 6 and Comparison Examples 1 to 4

In these Examples, whiteness was evaluated as follows Antibacterial zeolite was blended with each organic polymer to obtain a plate. Hunter whiteness on each plate was determined with a TC-1 type colorimeter, ex Tokyo Densyoku Industry Inc.

Antibacterial properties were evaluated by determining a Minimum Inhibitory Concentration (MIC) to *Escherichia coli, Pseudomonas aeruginosa* or *Aspergillus niger.*

A drop method for evaluating antibacterial properties was carried out as follows:

(1) *Escherichia coli,* IFO-12734, was used as a test strain.
(2) Preparation of fungi-liquid; the test strain which had been cultured in agar medium at 37° C. for 18 hours was suspended in a phosphoric acid salt buffer solution, pH 7.2, to obtain a suspension having a concentration of $10^8$ cells/ml.
(3) Determination; the aforesaid fungi-liquid was diluted to prepare a fungi-liquid having an initial fungi concentration of $2.9 \times 10^5$ cells/ml. Subsequently, this fungi-liquid was added dropwise to the surface of the polyester resin plate as mentioned below. This was maintained at 25° C.±5° C. for 6 hours. The number of fungi was counted on the fungi-liquid on the plate. The same procedures were repeated on an ABS resin plate, with the proviso that an initial fungi concentration was $1.8 \times 10^5$ cells/ml.

Supporting of Antibacterial Metals (Ion Exchange)

2000 g of commercial A-type zeolite, ex Ethyl Company, average particle size of 2.0 μm, were dispersed in 10 liters of demineralized water. After the dispersion was boiled for 1 hour, filtration and washing were sufficiently carried out. The A-type zeolite thus obtained was used as a starting material.

The A-type zeolite which was boiled and washed as mentioned above was put in a reaction vessel provided with a stirring apparatus having a content volume of 20 liters and was dispersed in demineralized water at room temperature to obtain 10 liters of slurry. Stirring was continued at a stirring speed of 500 rpm (initial pH of 11). Next, an aqueous 10% nitric acid solution was gradually added to the slurry to adjust its pH to 5.5. After 30 minutes with the stirring, a solution of 120 g of silver nitrate ($AgNO_3$, Ag amount of 3.8% by weight based on the zeolite) and 700 g of zinc nitrate ($Zn(NO_3)_2 \cdot 6H_2O$, Zn amount of 7.7% by weight based on the zeolite) in 5 liters of demineralized water, i.e., ion-exchange reaction liquid, was gradually added to the slurry over 30 minutes. The temperature was then raised to 65° C. and the stirring was continued for further 5 hours before end of the ion-exchange reaction of the antibacterial metals, followed by solid-liquid separation with a Buchner filtration unit. After washed with demineralized water, the solid phase was dried at 130° C. for 4 hours and aggregates were crushed. Antibacterial zeolite with high whiteness was obtained.

Preparation of a Surface-Treating Agent

<Preparation of Component (B), Organopolysiloxane Having a Basic Nitrogen Atom>

3990 grams of polymethylhydrogen siloxane (PS-118, trade mark, ex Chisso Corporation, a molecular weight of 360 to 420) and 1650 grams of N-(2-aminoethyl)-3-aminopropyltrimethoxysilane (S320, trade mark, ex Chisso Corporation) were mixed with each other and the mixture was heated at 140° C. for 6 hours to obtain organopolysiloxane having amino groups (nitrogen content of 3.7% by weight).

<Preparation of a Composition Comprising Components (A), (B) and (C)>

Preparation Example 1

700 parts by weight of phenyltrimethoxysilane and 300 parts by weight of decyltrimethoxysilane as component (A), 200 parts by weight of the organopolysiloxane having amino groups prepared above as component (B) and 50 parts by weight of acetic acid as component (C) were mixed with each other and the mixture was heated at 90° C. for 3 hours to obtain a transparent solution (surface-treating agent (i)).

Preparation Example 2

700 parts by weight of phenyltrimethoxysilane and 300 parts by weight of decyltrimethoxysilane as component (A), 500 parts by weight of the organopolysiloxane having amino groups prepared above as component (B) and 80 parts by weight of acetic acid as component (C) were mixed with each other and the mixture was heated at 90° C. for 3 hours to obtain a transparent solution (surface-treating agent (ii)).

The properties of the aforesaid surface-treating agent (ii) were as follows:

(1) specific gravity at 25° C. with a gravimeter: 1.018
(2) viscosity at 25° C. with a B type viscometer: 10 centipoises
(3) dispersing property in water, diluted 15 times: present stably for 2 hours as white emulsion.

<Preparation of a Surface-Treating Agent for Comparison>

Preparation Example 3

500 parts by weight of decyltrimethoxysilane, 500 parts by weight of the organopolysiloxane having amino groups prepared above as component (B) and 80 parts by weight of acetic acid as component (C) were mixed with each other and the mixture was heated at 90° C. for 3 hours to obtain a transparent solution (surface-treating agent (iii)). This surface-treating agent does not contain a hydrolyzable silane and/or a hydrolyzable oligomer thereof having an aryl group.

Treatment of Antibacterial Zeolite with a Surface-Treating Agent

In each Example or Comparison Example, 1000 parts by weight of the aforesaid antibacterial zeolite were dispersed in 3000 parts by weight of demineralized water to form slurry which was then stirred at a stirring speed of 500 rpm while maintained at a temperature of 30° C. (initial pH of 10). Subsequently, an aqueous 10% nitric acid solution was gradually added to this slurry to adjust its pH to 5.5. After the pH was confirmed not to change for at least one hour without further replenishing the aqueous nitric acid solution, to the slurry was added gradually over one hour an emulsion of each surface-treating agent which emulsion had been prepared by mixing the amount indicated in Table 1 (part by weight, before mixed with water) with demineralized water of 14 times weight as much as that of the agent. Further, the slurry was stirred at this temperature for 48 hours before end of the surface treatment. After solid-liquid separation with a Buchner filtration unit and subsequent washing of the solid phase with demineralized water, the solid phase was dried at 210° C. for 12 hours and aggregates were crushed. In each case, surface-treated antibacterial zeolite with high whiteness was obtained.

Blending to an Organic Polymer

As the organic polymer, use were made of three kinds of resins, ABS resin (Tufflex 410, trade mark, Monsanto Chemical Company Ltd.), polyamide resin (6N-SD, trade mark, Kanebo Ltd.), and polyester resin (PET-SD, trade mark, Kanebo Ltd.). Each of the aforesaid surface-treated antibacterial zeolites or untreated zeolite, and each of the aforesaid resins were used after pre-dried at 105° C. for 2 hours. The amount of the antibacterial zeolite was set to 2.0% by weight of the resin.

The aforesaid antibacterial zeolite and each of the resins were supplied to an injection molding machine (MODEL IS-EPN type, Toshiba Mechanical Company Ltd.) to mold a plate of 50 mm×90 mm×5 mm. The injection molding temperature was set as follows: 260° C. for the ABS resin, 270° C. for the polyamide resin and 285 ° C. for the polyester resin.

In Control 1, the aforesaid procedures were repeated to mold a resin plate, with the proviso that no antibacterial zeolite was blended.

Antibacterial properties of the antibacterial zeolite after surface-treated as mentioned above, the results of a Drop method for evaluating antibacterial properties and a Hunter whiteness on each plate are as shown in Table 1.

TABLE 1

|  | Example | | | | | | Comparison Example | | | | Contr. |
| --- | --- | --- | --- | --- | --- | --- | --- | --- | --- | --- | --- |
|  | 1 | 2 | 3 | 4 | 5 | 6 | 1*1 | 2 | 3 | 4 | 1*2 |
| Antibacterial zeolite, part by weight | 1000 | 1000 | 1000 | 1000 | 1000 | 1000 | 1000 | 1000 | 1000 | 1000 | — |
| Surface-treating agent, part by weight | 5 | 20 | 40 | 80 | 160 | 40 | — | 240 | 40 | 40 | — |
| Type of the surface-treating agent | (i) | (i) | (i) | (i) | (i) | (ii) | — | (i) | (iii) | B*3 | — |
| MIC, ppm |  |  |  |  |  |  |  |  |  |  |  |
| E. coli | 125 | 125 | 125 | 125 | 125 | 125 | 125 | 250 | 125 | 125 | — |
| P. aeruginosa | 125 | 125 | 125 | 125 | 125 | 125 | 125 | 500 | 125 | 125 | — |
| A. niger | 250 | 250 | 250 | 250 | 500 | 250 | 250 | 2000 | 250 | 250 | — |

TABLE 1-continued

|  | Example | | | | | | Comparison Example | | | | Contr. |
|---|---|---|---|---|---|---|---|---|---|---|---|
|  | 1 | 2 | 3 | 4 | 5 | 6 | 1*1 | 2 | 3 | 4 | 1*2 |
| Drop method for evaluating antibacterial properties, cells/ml | | | | | | | | | | | |
| ABS resin | 0 | 0 | 0 | 0 | 0 | 0 | 0 | 30 | 0 | 0 | $2.7 \times 10^5$ |
| Polyester resin | 0 | 0 | 0 | 0 | 0 | 0 | 0 | 10 | 0 | 0 | $3.1 \times 10^5$ |
| Hunter whiteness | | | | | | | | | | | |
| ABS resin | 17.6 | 36.1 | 41.2 | 41.1 | 41.5 | 41.8 | 11.3 | 41.8 | 23.6 | 28.1 | 42.0 |
| Polyamide resin | 49.7 | 68.3 | 74.0 | 76.0 | 76.2 | 75.9 | 43.6 | 76.0 | 62.7 | 64.3 | 76.4 |
| Polyester resin | 24.7 | 53.3 | 58.4 | 61.0 | 61.6 | 61.7 | 18.2 | 61.9 | 40.3 | 46.5 | 65.6 |

*1Use was made of antibacterial zeolite on which the surface treatment had not been carried out.
*2No antibacterial zeolite was contained.
*3Only component (B) was used as a surface-treating agent.

In Examples 1 to 5, the amount of surface-treating agent (i) was increased within the range of the present invention. In Example 5, sufficient antibacterial properties were obtained though the antibacterial properties to *Aspergillus niger* was somewhat low. Hunter whiteness of each resin was improved, compared to that in Comparison Example 1. In Example 6, the amounts of components (B) and (C) were varied within the range of the present invention with surface treating agent (ii). Good antibacterial properties and high whiteness were exhibited which were almost same as those in Example 3. Control 1 was to determine antibacterial properties and Hunter whiteness on the resins having no antibacterial zeolite.

Meanwhile, in Comparison Example 1, zeolite which had not been surface-treated was used. Hunter whiteness was remarkably low, compared to Examples 1 to 5. In Comparison Example 2, the amount of surface-treating agent (i) exceeded the range of the present invention. Hunter whiteness was good, but the antibacterial properties decreased. In Comparison Example 3, use were made of 4% by weight of surface-treating agent (iii) which did not contain any silane having an aryl group. The antibacterial properties were good, but Hunter whiteness was low, compared to Example 3. In Comparison Example 4, component (B) was used as a surface-treating agent. Hunter whiteness was low, compared to Example 3.

Each of these plates was put in direct sunshine by a window in a room for 3 months with periodical observation. The plates of the present invention showed almost no change in whiteness and maintained their initial whiteness as observed immediately after the molding.

Examples 7 to 9
Supporting of Antibacterial Metals (Ion Exchange)

Ion exchange was carried out using the compounds in the amount indicated below.

Example 7: 120 g of silver nitrate ($AgNO_3$, Ag amount of 3.8% by weight based on zeolite), 700 g of zinc nitrate ($Zn(NO_3)_2 \cdot 6H_2O$, Zn amount of 7.7% by weight based on zeolite) and magnesium nitrate ($Mg(NO_3)_2 \cdot 6H_2O$, Mg amount of 2.0% by weight based on zeolite).

Example 8: 120 g of silver nitrate ($AgNO_3$, Ag amount of 3.8% by weight based on zeolite), 700 g of zinc nitrate ($Zn(NO_3)_2 \cdot 6H_2O$, Zn amount of 7.7% by weight based on zeolite) and 240 g of calcium nitrate ($Ca(NO_3)_2 \cdot 4H_2O$, Ca amount of 2.0% by weight based on zeolite).

Example 9: 120 g of silver nitrate ($AgNO_3$, Ag amount of 3.8% by weight based on zeolite), 700 g of zinc nitrate ($Zn(NO_3)_2 \cdot 6H_2O$, Zn amount of 7.7% by weight based on zeolite) and 140 g of aluminum nitrate ($Al(NO_3)_3 \cdot 9H_2O$, Al amount of. 0.5% by weight based on zeolite).

Treatment of Antibacterial Zeolite with a Surface-Treating Agent

The same treatment as in Examples 1 to 6 was repeated. As the surface-treating agent, use was made of surface-treating agent (i), in the amount indicated in Table 2 in part by weight.

Blending to an Organic Polymer

As the organic polymer, use was made of the same polyester resin as in Examples 1 to 6. The same procedures were repeated as in Examples 1 to 6 to prepare plates.

The results of a Drop method for evaluating antibacterial properties on the surface-treated antibacterial zeolite and the Hunter whiteness on the plates are as shown in Table 2.

TABLE 2

|  | Example | | |
|---|---|---|---|
|  | 7 | 8 | 9 |
| Antibacterial zeolite, part by weight | 1000 | 1000 | 1000 |
| Surface-treating agent, part by weight | 40 | 40 | 40 |
| Type of the surface-treating agent | (i) | (i) | (i) |
| Drop method for evaluating antibacterial properties, cells/ml | | | |
| Polyester resin | 0 | 0 | 0 |
| Hunter whiteness | | | |
| Polyester resin | 64.7 | 62.0 | 63.1 |

In Examples 7 to 9, use were made of the zeolites in which non-antibacterial metals, i.e., magnesium, calcium and aluminum were used, too. It was found that Hunter whiteness could be increased while maintaining comparable antibacterial properties, compared to Example 3 in which the amounts of silver and zinc and the amount of the surface-treating agent were same as in Examples 7 to 9.

These plates were put in direct sunshine by a window in a room for 3 months with periodical observation. The plates showed almost no change in whiteness and maintained their initial whiteness as observed immediately after the molding.

The present antibacterial zeolite has a remarkably less action of discoloring an organic polymer under the influence of heat during processing or under ultraviolet light such as the sunshine, when it is blended with the polymer. It also has good antibacterial properties.

What is claimed is:

1. An antibacterial zeolite exhibiting a less discoloring action, obtained by treating the surface of zeolite supporting an antibacterial metal selected from the group consisting of silver, copper, zinc, mercury, tin, lead, bismuth, cadmium, chromium, cobalt, nickel or a combination of two or more thereof, with 0.5 to 20% by weight, based on said zeolite, of a composition comprising (A) 100 parts by weight of a hydrolyzable silane and/or oligomer thereof of the formula:

wherein $R^1$ independently represents a $C_1$ to $C_{18}$ saturated alkyl group, aryl group or aralkyl group; $R^2$ independently represents a $C_1$ to $C_6$ saturated alkyl group; and n is 1 or 2, wherein at least 10% by weight of component (A) has an aryl group; (B) 1 to 1000 parts by weight of an organopolysiloxane having a basic nitrogen atom, of the formula:

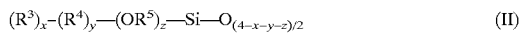

wherein $R^3$ independently represents a hydrogen atom or a $C_1$ to $C_8$ saturated alkyl group; $R^4$ independently represents an N-substituted or unsubstituted aminoalkyl group; $R^5$ independently represents a hydrogen atom or $C_1$ to $C_6$ saturated alkyl group; X, Y and Z are averaged values, X is 0 to 3, Y is 0.01 to 1, Z is 0 to 3, and the sum of X, Y and Z is 3.4 or less; and (C) 0.2 to 250 parts by weight of an acid which is soluble in water and which can form a salt with the organopolysiloxane of component (B).

2. The antibacterial zeolite claimed in claim 1, wherein said zeolite supporting an antibacterial metal supports at least one metal selected from the group consisting of sodium, potassium, magnesium, calcium, aluminum, titanium and cerium in addition to the antibacterial metal.

3. The antibacterial zeolite claimed in claim 1, wherein component (A) has a molecular weight of about 600 or less (multipled in the case of an oligomer).

4. The antibacterial zeolite claimed in claim 1, wherein $R^2$ is a methyl, ethyl or propyl group.

5. The antibacterial zeolite claimed in claim 1, wherein X is 0 to 2, Y is 0.1 to 0.6, and Z is 0 to 0.8.

6. A process for the preparation of the antibacterial zeolite claimed in claim 1, wherein the process comprises the steps of preparing an aqueous emulsion of the composition described in claim 1, treating the surface of zeolite supporting an antibacterial metal with the emulsion, and then drying the zeolite at a temperature of not lower than 200° C.

7. The process for the preparation of the antibacterial zeolite claimed in claim 6, wherein the antibacterial zeolite is for use in a blend with a polymer and the drying temperature is not lower than a melting point of the polymer to be blended and not higher than 500° C.

8. The process for the preparation of the antibacterial zeolite claimed in claim 6, wherein the drying temperature is not lower than a kneading temperature of the zeolite with the polymer and not higher than 500° C.

* * * * *